US00PP23346P3

(12) United States Plant Patent

Deng et al.

(10) Patent No.: US PP23,346 P3

(45) Date of Patent: Jan. 22, 2013

(54) *GERBERA* PLANT NAMED 'UFGE 4141'

(50) Latin Name: *Gerbera hybrida*
Varietal Denomination: UFGE 4141

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 12/931,572

(22) Filed: Feb. 4, 2011

(65) Prior Publication Data

US 2012/0204301 P1 Aug. 9, 2012

(51) Int. Cl.
*A01H 5/00* (2006.01)

(52) U.S. Cl. ..... Plt./357

(58) Field of Classification Search ..... Plt./357
See application file for complete search history.

*Primary Examiner* — Kent L Bell

(57) ABSTRACT

A new *Gerbera* plant particularly distinguished by having a novel combination of medium lengths of peduncles, semi-double orange-red inflorescence color, a moderate level of resistance to powdery mildew, and demonstrated potential to produce attractive plants in large (≧20-cm in diameter) containers, is disclosed.

3 Drawing Sheets

Genus and species: *Gerbera hybrida.*
Variety denomination: 'UFGE 4141'.

BACKGROUND OF THE NEW PLANT

The invention relates to a new and distinct variety of *Gerbera* plant named 'UFGE 4141'. The new *Gerbera* plant is a product of a planned breeding program conducted in Bradenton (up to February 2005) and Wimauma (since February 2005), Fla. 'UFGE 4141' originated from a cross made between 'UFGE 5-23' (unpatented) and 'UFGE 4-8' (unpatented) that was made during 2003 at Bradenton, Fla. 'UFGE 4141' was selected by the inventors from the progeny of the stated parentage in summer 2004 at Bradenton, Fla. The first asexual reproduction of 'UFGE 4141' was accomplished when crown division in fall 2004 in Bradenton, Fla., and subsequent reproduction of 'UFGE 4141' was by tissue culture. Plants of 'UFGE 4141' have been asexually propagated by crown division and tissue culture for more than four generations. Asexually propagated plants of 'UFGE 4141' have remained true to the original selected plant, and all characteristics of the plant have been transmitted and retained through four successive asexual vegetative generations.

Plant Breeder's Rights for this cultivar have not been applied for. 'UFGE 4141' has not been made publicly available more than one year prior to the filing of this application.

SUMMARY OF THE INVENTION

The new and distinct variety of *Gerbera* plant is characterized by a novel combination of medium lengths of peduncles, semi-double orange-red inflorescences, a moderate level of resistance to powdery mildew, and demonstrated potential to produce attractive plants in large (≧20-cm in diameter) containers. 'UFGE 4141' has not been observed under all possible environmental conditions. Its phenotype may vary significantly with variations in environment such as light intensity, temperature, and day length. The following are the most outstanding and distinguishing characteristics of this new cultivar when grown in Wimauma, Fla. under normal horticultural practices in greenhouse conditions which closely approximate those generally used in commercial practice.

1. Peduncle length of approximately 52 cm;
2. Semi-double inflorescence type;
3. Orange-red (RHS 33B) ray florets;
4. Yellow-green (RHS 150B) color discs before opening of disc florets;
5. Orange-red (RHS 33A) perianth lobe of disc florets;
6. Inflorescence head diameter of approximately 12 cm; and
7. Moderate resistance to powdery mildew.

DESCRIPTION OF THE PHOTOGRAPHS

This new *Gerbera* plant is illustrated by the accompanying photographs which show the plant's form, inflorescences, and foliage. The colors shown are as true as can be reasonably obtained by conventional photographic procedures. The photographs are of a plant approximately 5 months old which was produced from one tissue culture liner and is potted in a 2.7-L container.

DESCRIPTION OF THE NEW CULTIVAR

Figure 1:
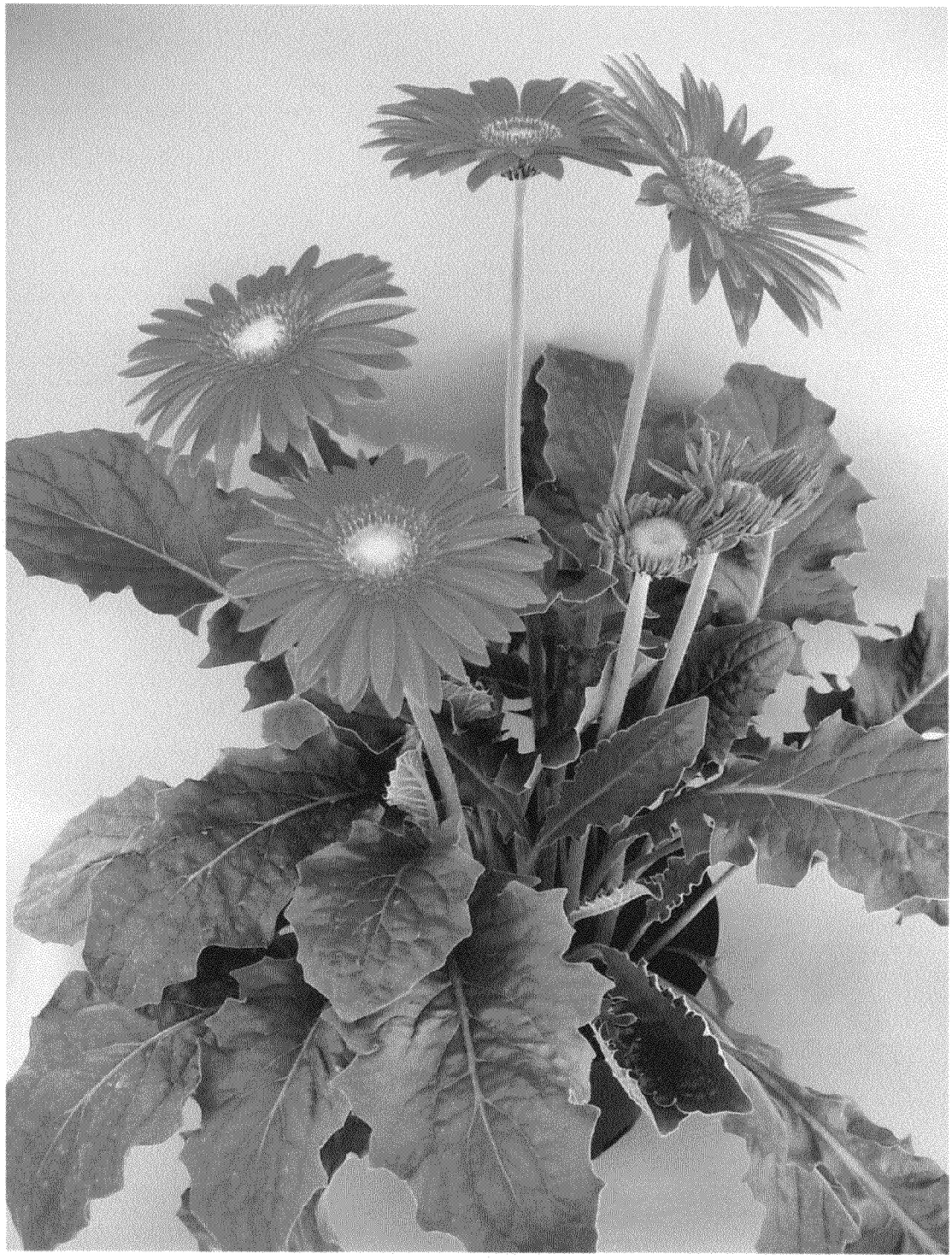
FIG. 1 shows the overall plant habit including inflorescences and foliage and is taken from a side perspective view.
Figure 2:
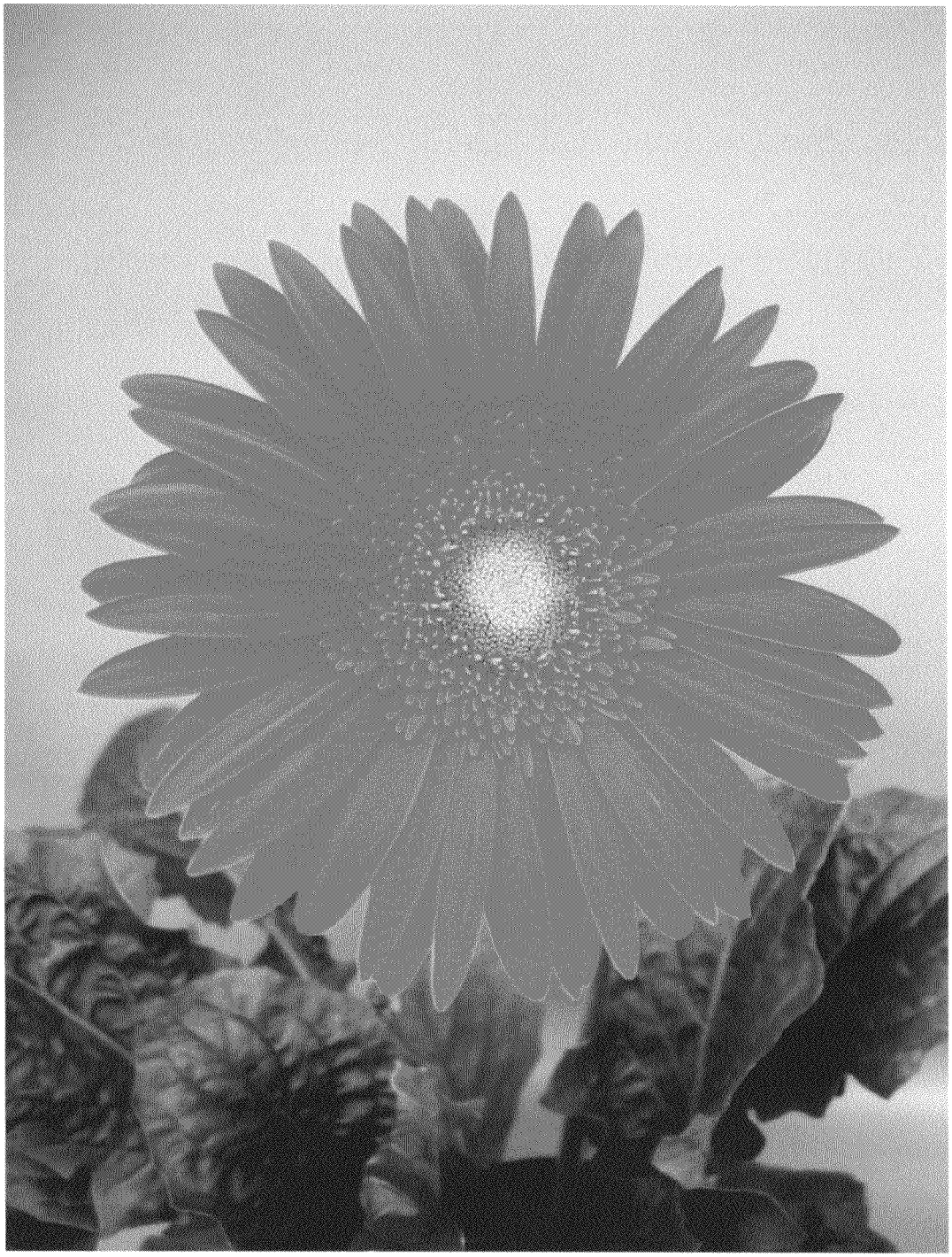
FIG. 2 shows a close-up of the inflorescences.
Figure 3:
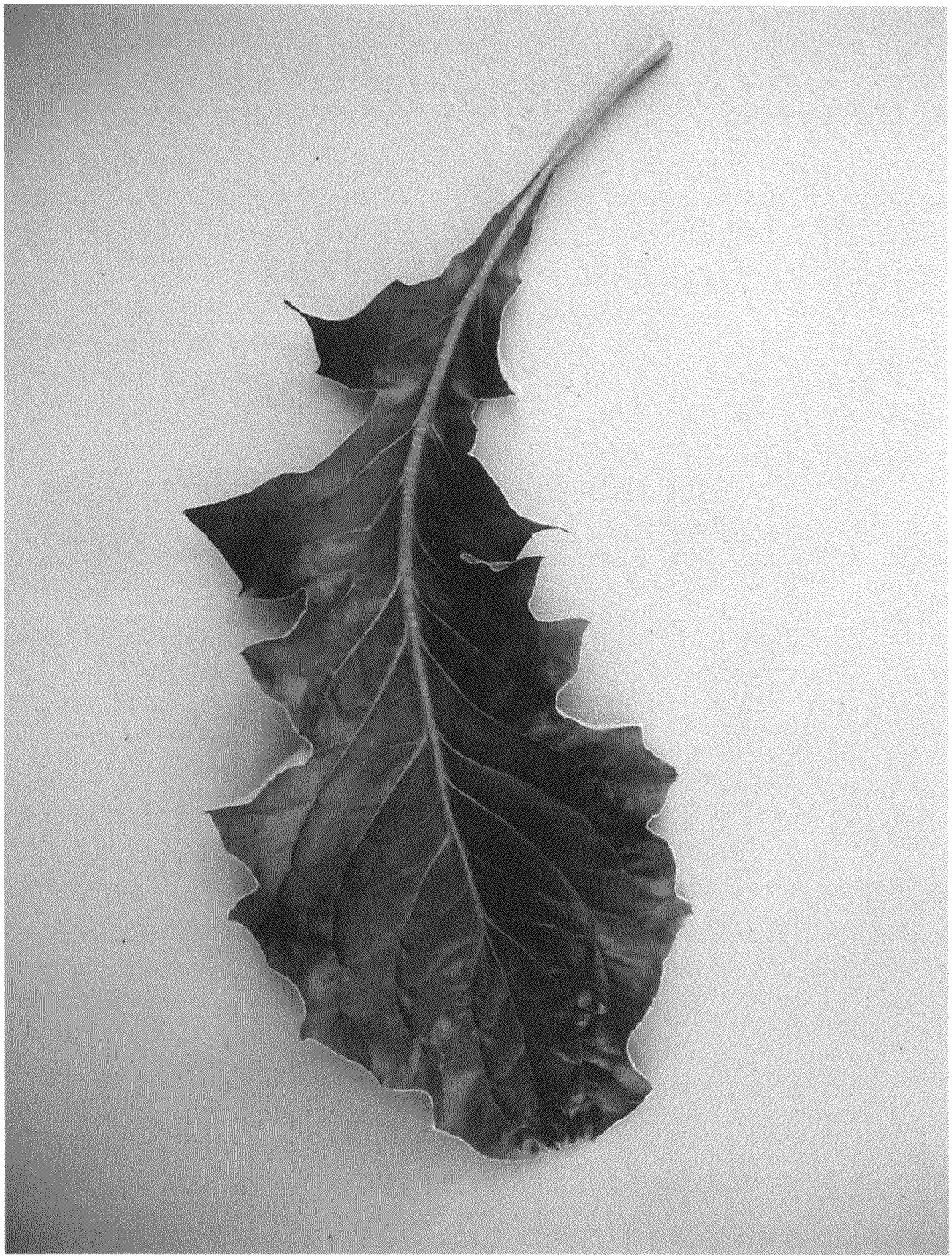
FIG. 3 shows a close-up of a typical leaf.

The following detailed description sets forth the distinctive characteristics of 'UFGE 4141'. The present botanical description is that of the variety at approximately 5 months old on Oct. 20, 2009 at 3:30 p.m. in a room under north light in Wimauma, Fla. The colors (except those in common terms) are described from R.H.S. Colour Chart published by The Royal Horticultural Society in London (1986 ed.), in association with the Flower Council of Holland.

DETAILED BOTANICAL DESCRIPTION

Classification:
*Botanical.—Gerbera hybrida* 'UFGE 4141'
*Common name.—Gerbera.* .

Parentage:

*Female, or seed, parent.*—'UFGE 5-23' (unpatented).

*Male, or pollen, parent.*—'UFGE 4-8' (unpatented).

Inflorescence:

*Appearance.*—Semi-double type inflorescence form; solitary inflorescences borne on upright and strong scapes above the foliar plane; ray and disc florets arranged acropetally on a capitulum.

*Diameter.*—About 12 cm.

*Color (general tonality from a distance of 3 meters).*—Bright orange-red (RHS 33B).

*Shape.*—Incurving funnel-shaped.

*Fragrance.*—None detected.

*Flowering season.*—Plants begin flowering about five weeks after planting and flower year-round in outdoor gardens in Wimauma, Fla., until plants are killed by frosts or freezes; plants flower year-round under greenhouse conditions in Wimauma, Fla.

*Inflorescence longevity.*—Inflorescences last about two to three weeks on the plant in Wimauma, Fla.; inflorescences not persistent.

*Quantity of inflorescences.*—Free flowering habit, with up to 10 open and developing inflorescences per plant at one time.

*Inflorescence bud.*—Height: About 1.2 cm. Diameter: About 2 cm. Shape: Oblate. Color (opening buds): Close to yellow-green (RHS 154A).

*Inflorescence size.*—Diameter: About 12 cm. Depth (height): About 1.7 cm. Diameter of disc: About 2 cm. Receptacle height: About 3 mm. Receptacle diameter: About 1.2 cm. Receptacle color: Close to green white (RHS 157A).

*Phyllaries.*—Number of phyllaries per inflorescence: About 55 arranged in about three whorls. Length: About 1.1 cm. Width: About 2 mm. Shape: Subulate. Apex: Narrowly acute. Base: Truncate. Margin: Entire. Texture, upper surface: Smooth, glabrous. Texture, lower surface: Moderately tomentose. Color, upper surface: Close to green (RHS 143C). Color, lower surface: Close to green (RHS 137D). Color towards the base: Close to green (RHS 137B).

*Inner ray florets.*—Number per inflorescence: About 59 arranged in about three whorls. Length: About 2.4 cm. Width: About 2 mm. Shape: Narrow elliptic. Apex: Emarginate to obtuse. Base: Truncate. Margin: Entire. Texture, upper surface: Smooth, glabrous, slightly velvety. Texture, lower surface: Smooth, glabrous, slightly velvety. Color: upper surface: Close to orange red (RHS 33B), but more intense orange. Color: lower surface: Close to orange (RHS 29A).

*Outer ray floret.*—Number: About 55 arranged in three whorls. Length: About 5.6 cm. Width: About 7 mm. Shape: Narrow elliptic. Apex: Emarginate to obtuse. Base: Truncate. Margin: Entire. Texture, upper surface: Smooth, glabrous, slightly velvety. Texture, lower surface: Smooth, glabrous, slightly velvety. Color, upper surface: Close to orange-red (RHS 33B) but more intense. Color, lower surface: Close to orange (RHS 25A) with streaks of orange (RHS 25D).

*Disc florets.*—Number: About 240. Length: About 1.7 cm. Width: About 5 mm. Shape: Tubular, fused. Apex: Narrowly obtuse. Base: Fused. Margin: Entire. Texture, upper and lower surfaces: Smooth, glabrous. Color: fully opened upper surface: Close to orange-red (RHS 34A). Color, fully opened lower surface: close to orange-red (RHS 30A). Color, fully opened mid-section: Close to yellow (RHS 9C). Color, fully opened base: Close to yellow (RHS 11C).

*Reproductive organs.*—Androecium: On disc floret only; quantity: one. Gynoecium: On both ray and disc florets; quantity per floret: one. Filament length: About 3 mm. Filament color: Close to yellow-orange (RHS 14C). Anther shape: Lanceolate. Anther length: About 4 mm. Anther width: About 1 mm. Anther color: Close to yellow-orange (RHS 14A). Pollen, amount: Scarce. Pollen color: Close to yellow (RHS 8C). Pistil, number per floret: One. Pistil length: About 1.3 cm. Stigma shape: Cleft. Stigma color: Close to yellow (RHS 12D). Style length: About 1.2 cm. Style color, distally: Close to orange-red (RHS 31D); proximally: close to yellow (RHS 9D). Ovary, color: Close to white (RHS 155A).

*Pappus.*—Quantity of hairs per floret: About 70. Length: About 7 mm. Diameter Less than 1 mm. Texture: Soft. Color: Close to yellow-white (RHS 158D).

*Peduncle.*—Length: About 52 cm. Tendency to fasciation: Absent. Diameter: About 6 mm; distally, about 4 mm. Strength: Strong. TextuTe: Densely tomentose. Color: Close to yellow-green (RHS 144B); distally, yellow-green (RHS 144D); proximally, tinged with red-purple (RHS 59A).

Plant:

*General appearance.*—Herbaceous perennial, typically grown as container or garden plants; upright and mounding growth habit, roughly globular in shape; leaves arranged in basal rosettes and outwardly arching; dense and bushy habit; inflorescences held above the foliar plane on erect and strong basal peduncles (or scapes); moderately vigorous.

*Plant height, soil level to top of foliar plane.*—About 35 cm.

*Plant height, soil level to top of inflorescence.*—About 56 cm.

*Plant width.*—About 65 cm.

*Foliage.*—Leaf arrangement: Basal rosette, alternate, simple. Leaf blade: Length: About 26 cm. Width: About 12 cm. Shape: Oblong. Apex: Obtuse. Margin: Irregular crenate, sinuses divergent, undulate. Texture, upper surface: Sparsely pubescent. Texture, lower surface: Moderately pubescent. Venation pattern: Pinnate. Color, upper surface: Close to yellow-green (RHS 146A). Color, lower surface: Close to yellow-green (RHS 146B). Glossiness on upper side: Medium. Shape of apex: Rounded.

*Petiole.*—Length: About 14 cm. Diameter: About 5.5 mm. Texture, upper and lower surfaces: Moderately pubescent. Color, upper surface: Close to yellow-green (RHS 144B). Color, lower surface: Close to yellow-green (RHS 144C).

Resistance to diseases: 'UFGE 4141' has been observed in multiple experiments in which it was compared with two common commercial cultivars, 'Pensacola' *gerbera* (unpatented) and 'Bimini' *gerbera* (unpatented), for the incidence and severity of powdery mildew, *Podosphaera* (syn. *Sphaerotheca*) *fusca* (Fr.) S. Blumer. 'UFGE 4141' has consistently been found to have a moderate level of resistance to powdery mildew. In two experiments conducted in 2008 and 2009 in Wimauma, Fla., tissue culture liners of 'UFGE 4141', 'Bimini', and 'Pensacola' were transplanted on into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Plants were grown under a plastic tunnel within a screen house with approximately 45% light exclusion. Fungicides were not applied throughout the experiments to subject the plants to natural powdery mildew disease pressures. In the first of the two powdery mildew experiments (Experiment 1), the severity of powdery mildew on *gerbera* leaves was assessed at week 8 after transplanting (Feb. 9, 2009), week 10 after transplanting (Feb. 18, 2009), week 12 after transplanting (Mar. 4, 2009), and week 14 after transplanting (Mar. 18, 2009). In the second of the two powdery mildew experiments (Experiment 2), the severity of powdery mildew was assessed at week 8 after transplanting (Oct. 15, 2009), week 10 after transplanting (Oct. 29, 2009), and week 12 after transplanting (Nov. 12, 2009). A randomized complete block design was used with five replications in Experiment 1 and with eight replications in Experiment 2. The experimental unit was a single containerized plant. 'UFGE 4141' showed a moderate level of resistance to powdery mildew in both Experiment 1 and Experiment 2 (Table 1). 'UFGE 4141' remained to be more productive than 'Bimini' and 'Pensacola' when natural powdery mildew disease pressure existed (Table 1). No other disease resistance characterizations have been made.

TABLE 1

Powdery mildew severity ratings and inflorescence counts of 'UFGE 4141' and two commercial gerbera cultivars, 'Bimini' and 'Pensacola', grown under natural powdery mildew pressure in two experimental trials in Wimauma, FL Experiment 1 (Winter 2008 through Spring 2009), Experiment 2 (Summer 2009 through Fall 2009)

| | PM Ratings[Z] | | | | Inflorescence |
|---|---|---|---|---|---|
| Cultivars | Week 8 | Week 10 | Week 12 | Week 14 | counts[Y] |
| | Experiment 1 (Winter 2008 through Spring 2009) | | | | |
| 'UFGE 4141' | 1.0 | 2.4 | 4.6 | 6.8 | 4.4 |
| 'Bimini' | 1.2 | 1.8 | 5.4 | 8.0 | 3.2 |
| 'Pensacola' | 1.0 | 2.0 | 4.8 | 8.6 | 3.0 |
| | Experiment 2 (Summer 2009 through Fall 2009) | | | | |
| 'UFGE 4141' | 1.1 | 3.5 | 5.3 | | 5.6 |
| 'Bimini' | 2.6 | 8.6 | 9.4 | | 2.6 |
| 'Pensacola' | 1.8 | 7.5 | 9.8 | | 1.1 |

[Z]Powdery mildew severity was rated on a scale of 1 to 10 as described by Hausbeck et al. (2002): 1 = no disease, 2 = trace to 10%, 3 = 10% to 20%, 4 = 20 to 30%, 5 = 30% to 40%, 6 = 40% to 50%, 7 = 50% to 60%, 8 = 60% to 70%, 9 = 70% to 80%, and 10 = 80% to 100% of leaf surface covered with powdery mildew.
[Y]Total number of inflorescences produced per plant over nine weeks from Jan. 20, 2009 to Mar. 17, 2009 in Experiment 1 or from Sep. 25, 2009 to Nov. 20, 2009 in Experiment 2, both in a screen house in Wimauma, FL.

COMPARISON WITH PARENTAL AND KNOWN CULTIVARS

'UFGE 4141' differs from the female parent 'UFGE 5-23' (unpatented) by having much shorter peducles, many more leaves, and denser foliage under growing conditions in Wimauma, Fla. than 'UFGE 5-23'. 'UFGE 4141' differs from the male parent 'UFGE 4-8' (unpatented) by having inflorescences that are red-orange and much larger under growing conditions in Wimauma, Fla. than 'UFGE 4-8'.

Comparisons were made with the commercial *gerbera* variety 'Bimini' (unpatented) and the commercial *gerbera* variety 'Pensacola' (unpatented). Two experiments were conducted in a greenhouse at Wimauma, Fla. under standard greenhouse management practices to evaluate the plant performance (days to inflorescence, inflorescence quality, inflorescence count, and plant quality) of 'UFGE 4141' for container plant production in comparison to 'Bimini' and 'Pensacola'. In the first of the two plant performance experiments (Experiment 3), tissue culture liners were transplanted on Dec. 9, 2008 into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Potted plants were grown on metal benches in a glass house and spaced 46 cm×46 cm apart. Temperatures inside the greenhouse ranged from 18° C. to 33° C. Two hours of additional photoperiodic lighting were provided between Dec. 9, 2008 and Mar. 17, 2009. Fungicides and insecticides were applied as needed to control powdery mildew and western flower thrips. Inflorescence quality was rated on a 1 to 5 scale: 1=very poor, 3=fair, some blemishes, but acceptable, and 5=excellent, bright, uniform, and no blemishes. Inflorescence counts were recorded weekly from Jan. 20, 2009 through Mar. 17, 2009. Plant quality was rated three times, on Jan. 20, 2009, Feb. 3, 2009, and Feb. 17, 2009, using a 1 to 5 scale: 1=few leaves or long petioles, container surface visible, very poor and unacceptable as flowering pot plants, 3=fair and marketable, and 5=excellent, full, symmetrical, attractive plants.

In the second of the two plant performance experiments (Experiment 4), tissue culture liners were transplanted on Aug. 13, 2009 into 2.7-L plastic containers filled with commercial potting mix amended with controlled release fertilizer at the rate of 5.28 $kg \cdot m^{-3}$ and trace element fertilizer at the rate of 1.05 $kg \cdot m^{-3}$. Plants were grown on metal benches in a greenhouse with a spacing of 46 cm×46 cm. The greenhouse was covered with aluminum shading cloth with approximately 30% light exclusion. Greenhouse temperatures ranged from 21° C. to 35° C. Two hours of additional photoperiodic lighting was provided beginning Sep. 15, 2009. Fungicides and insecticides were applied as needed to control powdery mildew and western flower thrips. Inflorescence quality and plant quality were rated as above for Experiment 3, but on Sep. 25, 2009, Oct. 15, 2009, and Nov. 5, 2009. The number of inflorescences produced per plant was recorded weekly from Sep. 25, 2009 through Nov. 20, 2009.

The experiment design for the plant performance experiments was a randomized complete block design with five replications in Experiment 3 and eight replications in Experiment 4. The experimental unit was a single containerized plant.

'UFGE 4141' came into flowering 26 to 31 days earlier than 'Bimini' and 'Pensacola' in Experiment 3 and 5 to 10 days earlier than 'Bimini' and 'Pensacola' in Experiment 4 (Table 2). Inflorescence quality ratings of 'UFGE 4141' were 3.8 to 4.2, similar to that of 'Pensacola', but it was lower than that of 'Bimini' (Table 2). In both Experiment 3 and Experiment 4, 'UFGE 4141' produced more inflorescences (87% to 144% more than 'Bimini' and 300% more than 'Pensacola') (Table 2). The plant quality rating of 'UFGE 4141' was 3.7 and 4.4 in Experiment 3 and Experiment 4, respectively, higher than that of the controls (Table 2).

TABLE 2

Plant performance of 'UFGE 4141' and two commercial cultivars, 'Bimini' and 'Pensacola' grown in Experiment 3 (Winter 2008 through Spring 2009) and Experiment 4 (Summer 2009 through Fall 2009) in Wimauma, Florida.

| Cultivars | Days to 1st open flowers (no.) | Inflorescence quality[Z] | Inflorescence counts[Z] (no.) | Plant quality[Y] |
|---|---|---|---|---|
| | Experiment 3 (Dec. 9, 2008 to Mar. 17, 2009) | | | |
| 'UFGE 4141' | 37.8 | 3.8 | 5.6 | 3.7 |
| 'Bimini' | 64.0 | 5.0 | 3.0 | 3.1 |
| 'Pensacola' | 68.8 | 4.1 | 1.4 | 3.3 |
| | Experiment 4 (Aug. 13, 2009 to Nov. 20, 2009) | | | |
| 'UFGE 4141' | 44.6 | 4.2 | 11.9 | 4.4 |
| 'Bimini' | 50.1 | 4.8 | 5.5 | 3.2 |
| 'Pensacola' | 55.8 | 4.3 | 2.5 | 3.3 |

[Z]Inflorescence count data were collected over nine weeks from Jan. 20, 2009 to Mar. 17, 2009 in Experiment 3 and another nine weeks from Sep. 25, 2009 to Nov. 20, 2009 in Experiment 4. Each value represents the mean of five (Experiment 3) or eight (Experiment 4) replicates.

TABLE 2-continued

Plant performance of 'UFGE 4141' and two commercial cultivars, 'Bimini' and 'Pensacola' grown in Experiment 3 (Winter 2008 through Spring 2009) and Experiment 4 (Summer 2009 through Fall 2009) in Wimauma, Florida.

| Cultivars | Days to 1st open flowers (no.) | Inflorescence quality[Z] | Inflorescence counts[Z] (no.) | Plant quality[Y] |
|---|---|---|---|---|

[Y]The plant quality rating value in Experiment 3 was the mean of five replicates over three times (January 20, February 3, and Feb. 17, 2009), and the plant quality rating value in Experiment 4 was the mean of eight replicates over three times (September 25, October 15, and Nov. 5, 2009).

Literature Cited

Hausbeck, M. K., W. R. Quackenbush, and S. D. Linderman. 2002. Evaluation of cultivars of African daisy for resistance to powdery mildew, 2002. B&C Tests 18:O0004.

We claim:

1. A new and distinct cultivar of *Gerbera* plant named 'UFGE 4141', as illustrated and described herein.

* * * * *